(12) United States Patent
Yee et al.

(10) Patent No.: US 7,878,973 B2
(45) Date of Patent: Feb. 1, 2011

(54) SINGLE USE LARYNGOSCOPE

(75) Inventors: Kevin Finehing Yee, Wahroonga (AU);
Mark Lloyd Graham Bennett, Kings Park (AU)

(73) Assignee: Anaesthesia Airways Pty Limited, Wahroonga NSW (AU)

( * ) Notice: Subject to any disclaimer, the term of this patent is extended or adjusted under 35 U.S.C. 154(b) by 1280 days.

(21) Appl. No.: 10/544,452

(22) PCT Filed: Feb. 11, 2004

(86) PCT No.: PCT/AU2004/000159

§ 371 (c)(1),
(2), (4) Date: Dec. 6, 2005

(87) PCT Pub. No.: WO2004/071285

PCT Pub. Date: Aug. 26, 2004

(65) Prior Publication Data

US 2006/0189847 A1 Aug. 24, 2006

(30) Foreign Application Priority Data

Feb. 11, 2003 (AU) ............... 2003100092
May 5, 2003 (AU) ............... 2003902127

(51) Int. Cl.
*A61B 1/267* (2006.01)
*A61B 1/06* (2006.01)

(52) U.S. Cl. .................. 600/199; 600/178; 600/118
(58) Field of Classification Search .............. 600/199, 600/200, 188, 185, 178–180, 118; 606/10; 362/572, 574
See application file for complete search history.

(56) References Cited

U.S. PATENT DOCUMENTS

| | | | | |
|---|---|---|---|---|
| 3,597,362 A | * | 8/1971 | Bollyky et al. | 252/700 |
| 3,598,113 A | * | 8/1971 | Moore et al. | 600/199 |
| 4,596,239 A | * | 6/1986 | Bauman | 600/197 |
| 4,858,620 A | * | 8/1989 | Sugarman et al. | 600/587 |
| 5,277,173 A | * | 1/1994 | Cantele | 600/191 |
| 5,320,269 A | * | 6/1994 | Deschenes et al. | 227/67 |
| 6,193,510 B1 | * | 2/2001 | Tsimerman | 433/29 |
| 2005/0080384 A1 | * | 4/2005 | Green | 604/218 |

* cited by examiner

*Primary Examiner*—John P Leubecker
(74) *Attorney, Agent, or Firm*—Davis & Bujold, P.L.L.C.

(57) ABSTRACT

A laryngoscope (10) to assist tracheal intubation on a patient, comprising a body having a handle (14), and a laryngoscope blade (12) extending from the handle (14); a lighting system (21) including a light source integrated in the laryngoscope body and arranged in use to be activated to adopt an operational mode to provide illumination to the patient's throat; control means operative to allow only a single occurrence of the lighting system in the operational mode; and wherein once activated in the operational mode, the lighting system provides illumination for only a limited time.

24 Claims, 11 Drawing Sheets

SINGLE USE LARYNGOSCOPE

This application claims priority under 35 U.S.C. §371 to International Application PCT/AU2004/000159, published as WO2004/071285 A1, the entire disclosure of which application is hereby incorporated herein by reference in its entirety, and claims foreign priority benefits under 35 U.S.C. §365(b) to Australian Patent Application Serial No. 2003100092, filed Feb. 11, 2003, and to Australian Patent Application Serial No. 2003902127, filed May 5, 2003, the entire disclosures of which applications are hereby incorporated herein by reference in their entirety.

TECHNICAL FIELD

The invention concerns a laryngoscope for use in laryngoscopy including tracheal intubation in a patient. The laryngoscope is intended for a single use after which it is to be discarded.

BACKGROUND ART

Laryngoscopes are currently used to assist tracheal intubation on a patient, for example, following induction of general anaesthesia and in advanced cardiopulmonary resuscitation.

Traditional laryngoscopes, including the battery casing and light source, are difficult to sterilise. Some blades with light fittings simply cannot be autoclaved. Some microbes are not destroyed by sterilisation posing a risk of cross infection between patients when reusing a laryngoscope. The sterilisation of a laryngoscope blade also reduces its functional life.

Disposable laryngoscope blades designed for single use have been manufactured to address these problems. These laryngoscopes, such as the *Welch Allyn* Expendable Layngoscopes (Model 69090), utilise a reusable pen light torch as a light source that inserts into the blade handle. After the laryngoscope has been used, the light source is removed so that it can be reused, and the blade and handle are discarded.

DISCLOSURE OF THE INVENTION

In a first aspect the present invention provides a laryngoscope to assist tracheal intubation on a patient, comprising a body having a handle, and a laryngoscope blade extending from the handle; a lighting system including a light source integrated in the laryngoscope body and arranged in use to be activated to adopt an operational mode to provide illumination to the patient's throat; control means operative to allow only a single occurrence of the lighting system in the operational mode; and wherein once activated in the operational mode, the lighting system provides illumination for only a limited time.

An advantage of this aspect of the invention is that the lighting system, which is integrated in the laryngoscope body, is designed only for a single use. As such, the lighting system operates as a safety feature as once the lighting system has expired, the laryngoscope is rendered useless and therefore the chances of it being reused are substantially reduced. Furthermore, by being unable to re-activate the lighting system in a used laryngoscope provides positive evidence that the laryngoscope has been used and therefore should be disposed of.

The period in which the light source remains active is preferably preselected by the manufacturer and is long enough to adequately cover the length of the surgical procedure in which the laryngoscope is used. It is desirable that the period of activation of the lighting system is not excessive as it may encourage secondary use of the laryngoscope and also lead to an unnecessary increase in the cost of manufacture of the instrument. Typically the length of period is in the order of one or a few hours.

The lighting system may provide illumination in the operational mode for a period in the order of one to three hours.

The control means may include an activation device that is operative to activate the lighting system to adopt the operational mode but is prevented from subsequently de-activating the lighting system.

The activation device may be in the form of an insulating tab which provides a break in the lighting system circuit, the tab includes an end which projects outside the laryngoscope body so that it can be manually removed and wherein once removed, the lighting system circuit is established thereby causing activation of the lighting system. Advantages of the insulating tab is that it provides an inexpensive one way switch and also it provides an indicator to a user as to whether the laryngoscope has been used. However, it needs to be appreciated that other types of one way switches may be used as will be appreciated by those skilled in the art.

The activation device may be in the form of a switch that incorporates a part that is movable on the laryngoscope body from a first position to a second position to activate the lighting system to adopt the operational mode, but is inhibited from movement from the second position to the first position.

The part may be formed as an end portion of the laryngoscope body.

The period of activation of the lighting system in the operational mode may be determined by the life of a power supply. The power supply, which typically is one or more batteries, is chosen so that its lifespan is commensurate with the desired length of activation of the lighting system.

The control means may include a limiting device operative to establish the length of period of illumination of the lighting system in the operational mode.

A power supply may be removable from the laryngoscope body.

The laryngoscope body may include a cover that allows access to the power supply, and wherein removal of the cover results in at least partial destruction of the body.

The cover may be arranged to be snap fitted onto a portion of the laryngoscope body.

The cover may be the movable part of the activation device.

The lighting system may be operative to adopt a test mode to allow for testing of the lighting system. After operation in the test mode it is still possible to operate the laryngoscope in the operational mode. However, it is only possible to activate the laryngoscope in the operational mode once. The test mode may be limited to a period of time that is too short to allow intubation of a patient.

When in the test mode, the light source may be illuminated.

The period the light source is able to remain illuminated in the test mode may be substantially shorter than in the operational mode.

The laryngoscope may further comprise an activating device that is operative to activate the lighting system to adopt the test mode.

The activation device may be operative to activate the lighting system to adopt both the test mode and the operational mode.

The lighting system may be operative to automatically change from the test mode to the operational mode after the lighting system has been in the test mode for a predetermined period.

The limiting device may control the period of illumination of the light source in the test mode and operational mode, and wherein when in the test mode, the period of illumination may be interrupted and recommenced at a later time, whereas in the operational mode, the limiting device prevents interruption of the illumination period thereby limiting the lighting system to a single occurrence in the operational mode.

The limiting device may be in the form of an electronic timer connected to the lighting system circuit.

The lighting system may further comprise a power supply that is locatable within the laryngoscope body.

The power supply may be locatable in the handle of the laryngoscope.

The power supply may be locatable in the blade of the laryngoscope.

The laryngoscope blade may incorporate a cavity in which the entire lighting system is housed, and the body may further include a cover arranged to be locked over the blade cavity so as to prevent access to the lighting system. Including the entire lighting system within the laryngoscope blade minimises the number of components used in the laryngoscope body. Further, the design of the handle can be dictated purely by functional aspects rather than needing to provide adequate space to incorporate components of the lighting system as in previous laryngoscope designs.

Various types of light sources may be incorporated within the lighting system. For example, the light source may be a light emitting diode (LED), a halogen bulb, a krypton bulb or a xenon bulb. In a preferred form, the light source is located in the laryngoscope blade. However, in another form the light source may be remote from the blade and a light guide may be provided to direct the emitted light to an outlet in the blade.

The angle between the handle and the blade may be approximately 75 degrees so that it is ergonomically easy to use.

At the end of the handle, the side closest to the blade may extend slightly toward the blade to form a slight hook shape. This hook extension enables easier handling of the laryngoscope.

It is an advantage of the invention that after the light system ceases to be active, the laryngoscope does not have the required functionality to be properly reused on a patient. As a result, the risk of cross contamination between patients through the reuse of laryngoscopes is greatly reduced. This disposable laryngoscope is a low cost alternative to traditional laryngoscopes, as the construction costs are lower and associated costs of sterilisation are removed. In this way, a clean and reliable laryngoscope is always ready for instant use.

BRIEF DESCRIPTION OF DRAWINGS

Embodiments of the present invention will now be described with reference to the accompanying drawings. It is to be appreciated that the particularity of the drawings and the related description does not supersede the preceding broad description of the invention.

In the drawings.

DETAILED DESCRIPTION OF THE DRAWINGS

Figure 1:
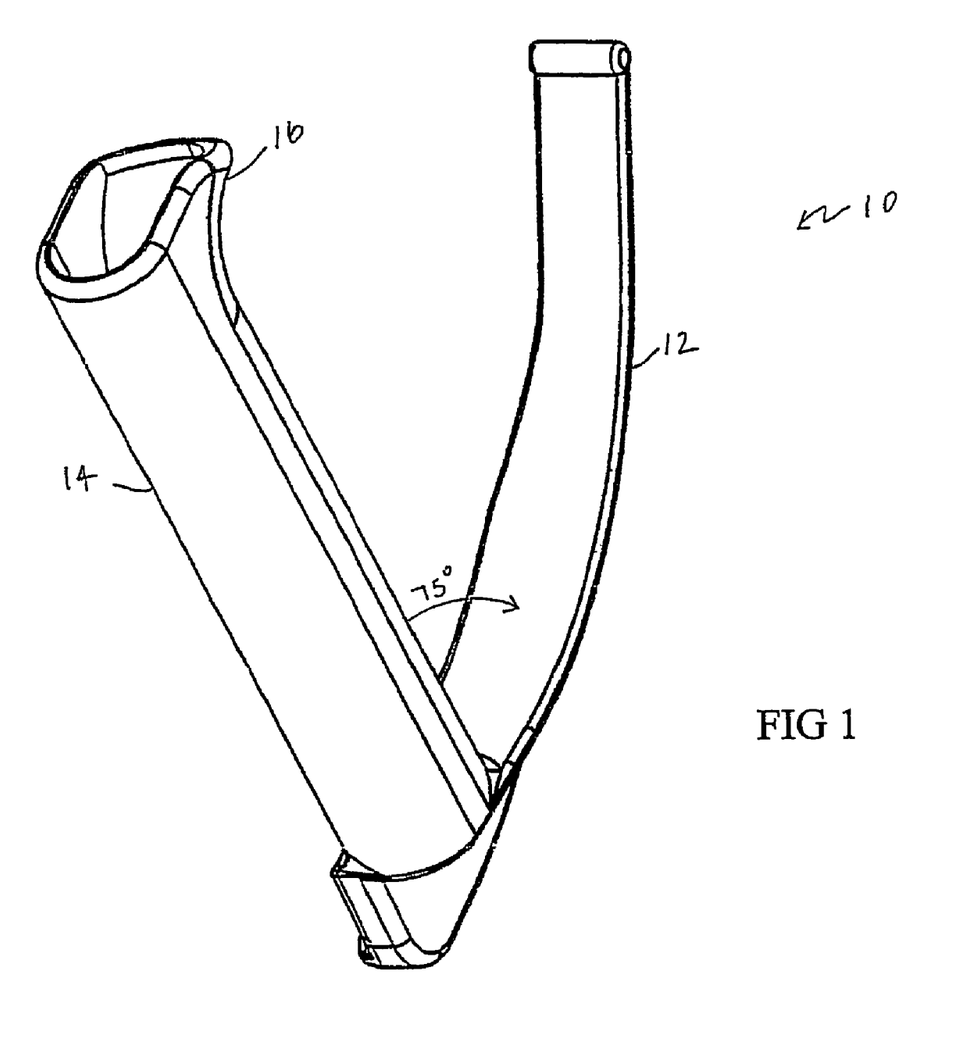
FIG. 1 is a perspective view of a first embodiment of a laryngoscope according to the invention.
Figure 2:
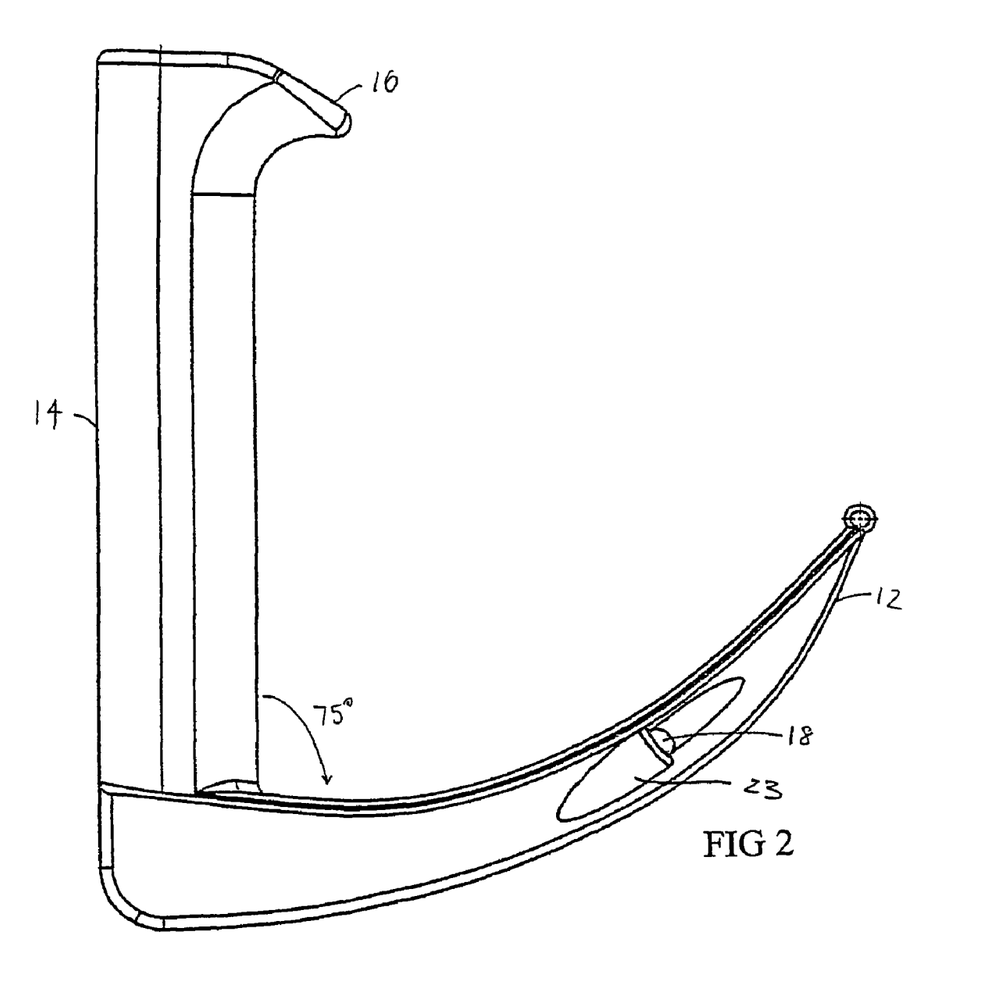
FIG. 2 is a side view of the laryngoscope of FIG. 1.

Referring to FIG. 1, a single use disposable laryngoscope 10 has a blade 12 and a handle 14 attached to one end of the blade 12. The body of laryngoscope 10 is a one-piece construction made from a hard plastic, that is strong enough to lift 15 kg and smooth enough to glide easily over the surface of the tongue.

The angle between the blade 12 and the handle 14 is 75 degrees so that it is ergonomically easy to use. This angle may be varied within about plus or minus 15 degrees. The handle 14 is approximately 12 centimeters in length.

The end of the handle 14 is shaped for easier handling. At the end of the handle, the side closest to the blade 16 extends slightly toward the blade 12, to form a slight hook shape. This hook extension 16 acts as a nudge against the index finger of a user gripping the handle 14 when lifting during laryngoscopy.

Figure 3:
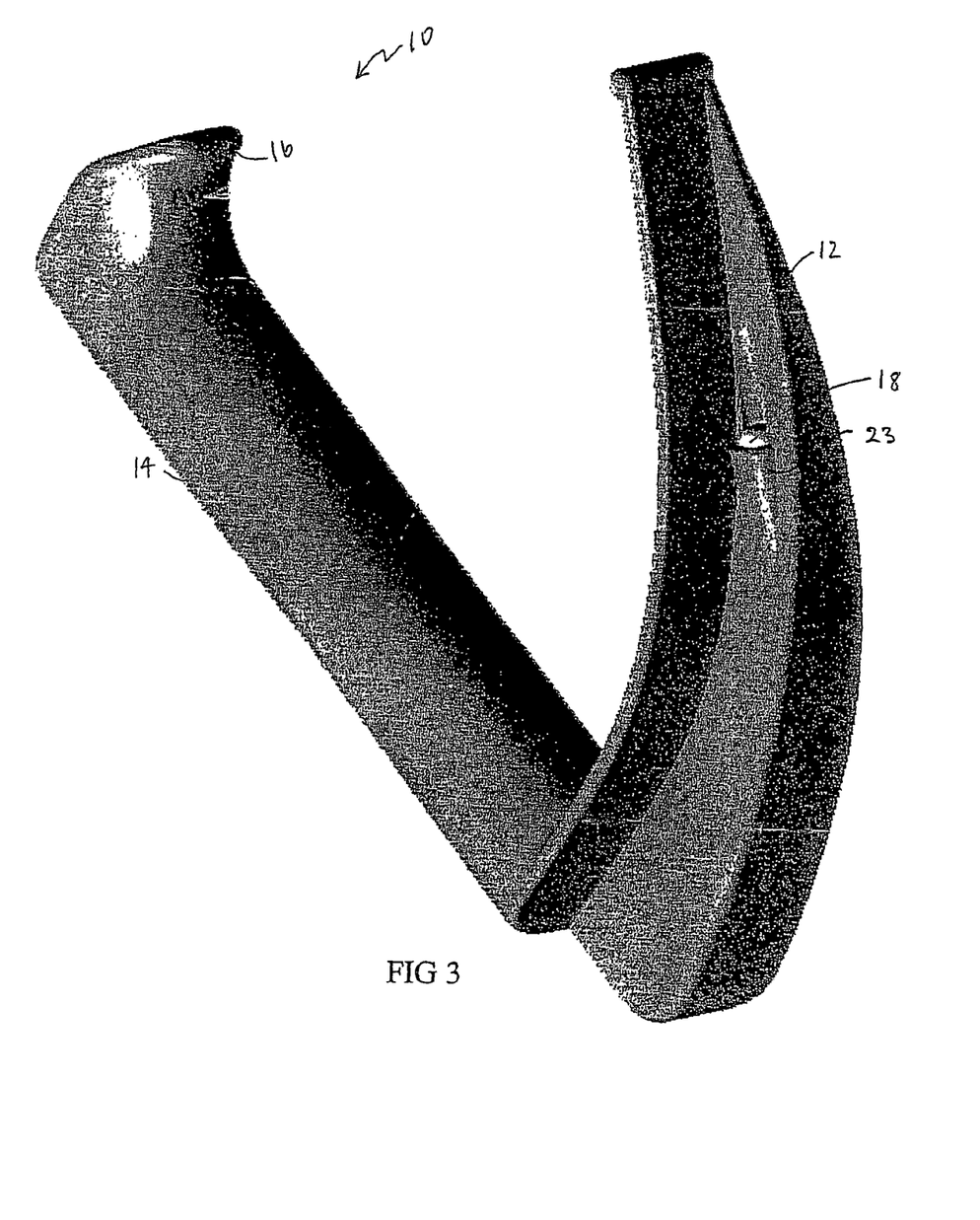
FIG. 3 is a further perspective view of the laryngoscope of FIG. 1.

As shown in FIG. 3, the blade 12 has a curvature similar to the Macintosh blade and has a 'Z' shaped cross section.

Figure 4:
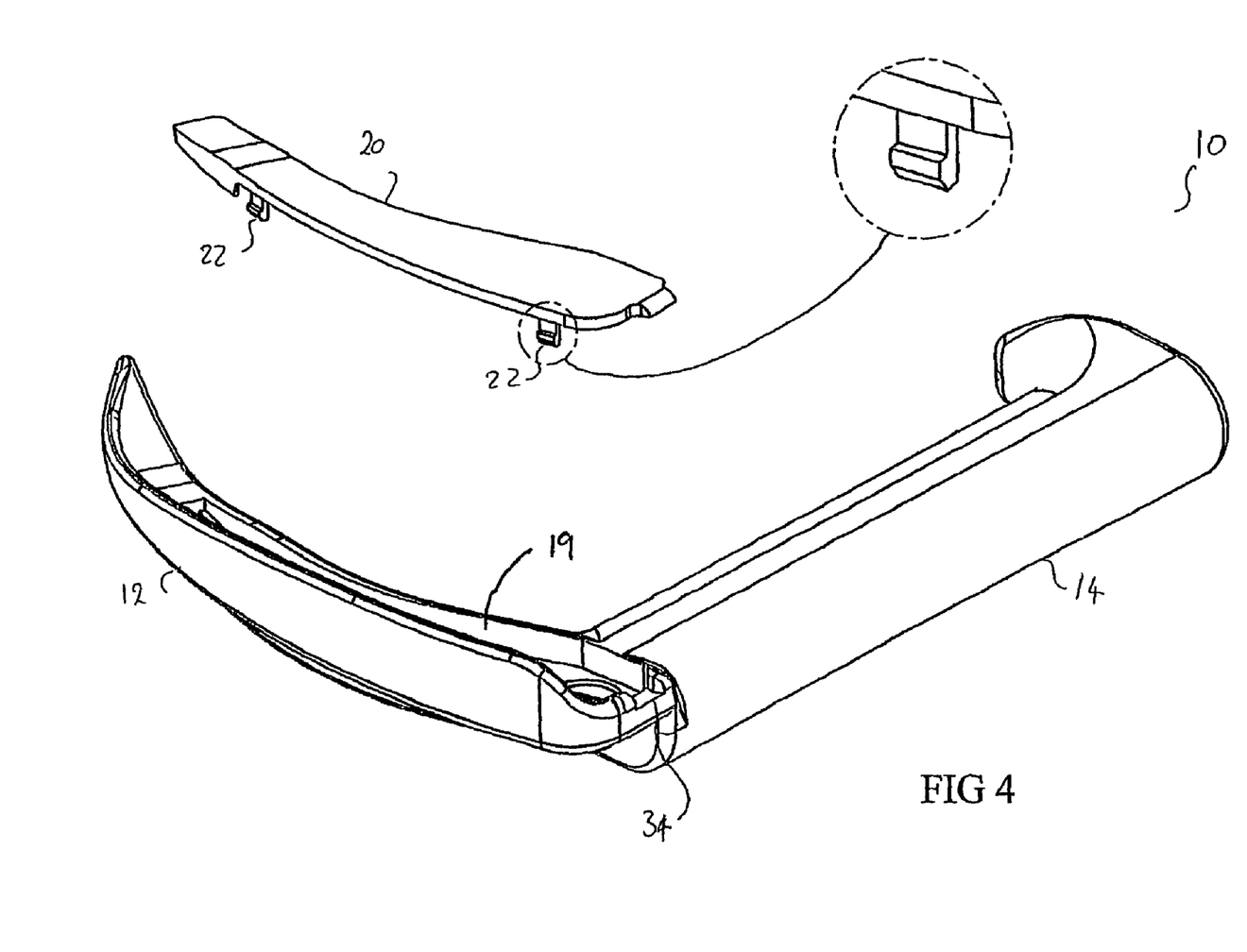
FIG. 4 is an exploded view of the laryngoscope of FIG. 1.

Referring to FIG. 4, the laryngoscope 10 includes a cavity 19 which is arranged to receive a lighting system 21 disclosed in more detail below. A snap on cover 20 locates over the cavity, and once fitted to blade 12, lugs 22 prevent subsequent removal of snap on cover 20.

Figure 5:
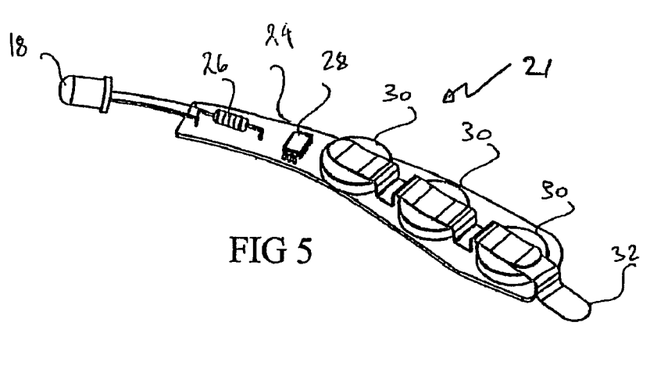
FIG. 5 is a perspective view of a lighting system which is housed within the laryngoscope of FIG. 1.
Figure 6:
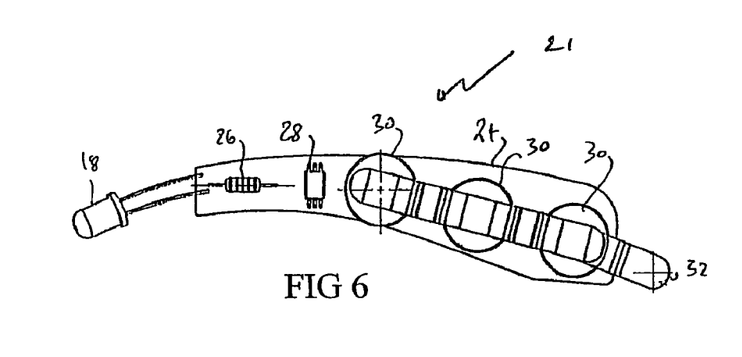
FIG. 6 is a plan view of the system of FIG. 5.

Referring to FIGS. 5 and 6, the lighting system 21 incorporates a populated circuit board 24 that is dimensioned to be fitted into blade cavity 19 and be retained by the snap on cover 20. The lighting system 21 includes an LED 18, a current limiting resistor 26, and three 3V batteries 30. The connection to one of the batteries is interrupted by an activating insulating tab 32 which forms a one way switch for the system 21 and which forms part of a control arrangement for the laryngoscope. Pulling out tab 32 completes the circuit and puts the laryngoscope into the operational mode causing the LED 18 to be illuminated. The control means further includes a time limiting device in the form of electronic timer 28 which operates to shut off power to LED 18 after a predetermined time such as one hour or a few hours. After power has been shut off the electronic timer 28 prevents it from being restored.

Electronic timer 28 may take any one of three forms as follows:

Timer circuit A-A programmable, time count micro controller and a relay are employed. The set operational period, one hour, is counted from the moment the light source is activated. The time tolerance is programmable to plus or minus 2 or 3 minutes, and a warning off/on flash is programmable to activate two minutes before the power is cut off. The relay can operate at 3 volts and has a fairly low consumption of current, around 600 mAmp.

Timer circuit B-A programmable micro controller and transistors are employed. This requires 1 resistor and 3 transistors to replace the relay of Timer circuit A. All other functions are identical. The current requirement would be roughly 3.6 volts and 650 mAmp. In either of timer circuit version A or B, once the time count micro controller has been activated, it cannot be activated again. This means that replacement of batteries does not allow the light source to be activated again following a single operational use.

Timer circuit C-A silicon-based microchip is employed and is surface mounted to the printed circuit board. The microchip has a number of integrated functions as follows:

the interruption of power to the laryngoscope's lamp after 60 minutes of operation:

initiation of a series of rapid flashes of the lamp 5 minutes before the pre-set time has elapsed the tolerance for the interruption of the power supply to plus or minus 2 minutes the low voltage cut-out of power to the lamp should the voltage produced by the battery fall to between 2.3 to 2.2 volts The microchip also includes a retaining memory or an electrical erasable memory, which ensures that if a new set of batteries is inserted by error or design into a laryngoscope that has already been used no power will be delivered to the light source. The microchip is supported by an external capacitor chip that is also surface mounted on the printed circuit board.

In all of the above timer circuit arrangements, removal and re-insertion of the batteries does not allow for re-activation of the light source in use. However, in one embodiment there is provided a test mode. In one form, an initial test period of 60 seconds is provided during which removal of the batteries will allow for subsequent activation upon re-insertion of the batteries. In another form, there may be provided a switch or the like that allows activation of the test mode. The test mode feature is provided to allow for testing of the laryngoscope before use, or to allow for momentary activation due to brief contact with the battery terminals at the time of inserting the batteries. The test period is limited to a short period of time that is insufficient to allow for intubation of a patient in the test mode.

Referring again to FIG. 4, when the lighting system 21 is fitted into the blade 12, the LED is mounted within a molded aperture 23 (FIG. 3) in the blade so as to illuminate light from the blade, and the insulating tab 32 protrudes from a slot 34 formed at the heel of the laryngoscope. This allows tab 32 to be grasped by a user to pull out to activate the LED.

Figure 7:
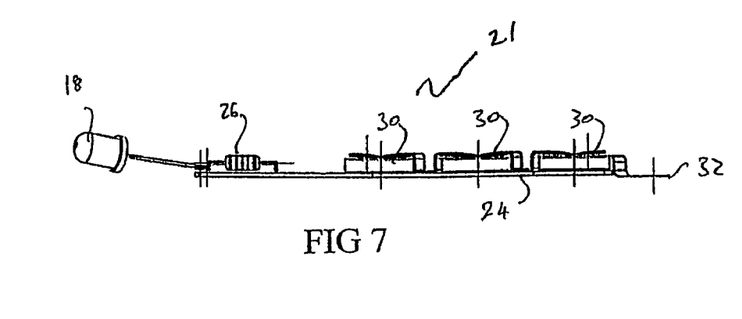
FIG. 7 is an elevation view of an alternative lighting system.

In an alternative arrangement the electronic timer 28 can be omitted as shown in FIG. 7. The light source will remain illuminated until the battery is drained of power. Again this can be limited to be a short time period of one hour or a few hours.

The laryngoscope 10 can be used to assist tracheal intubation. The light system of the laryngoscope 10 is switched on by removing tab 32. Once activated, the light source will remain illuminated for a fixed time. The blade 12 is then loaded with the appropriate endotracheal tube and intubation is performed in the usual manner. Once the light system becomes deactiveated, and the light source is no longer illuminated, the laryngoscope 10 is rendered useless and cannot be reused on another patient as the light system can no longer be activated. The entire unit is then disposed of, including the battery and light source.

Referring to FIGS. 8 to 14, an alternative embodiment of a laryngoscope 110 according to the invention is illustrated. Like parts to the first described embodiment are indicated with like reference numerals in the range 100-199. In this embodiment, the power source in the form of two AA or AAA batteries is mounted inside the handle 114. The laryngoscope is supplied with the batteries already present.

Figure 9:
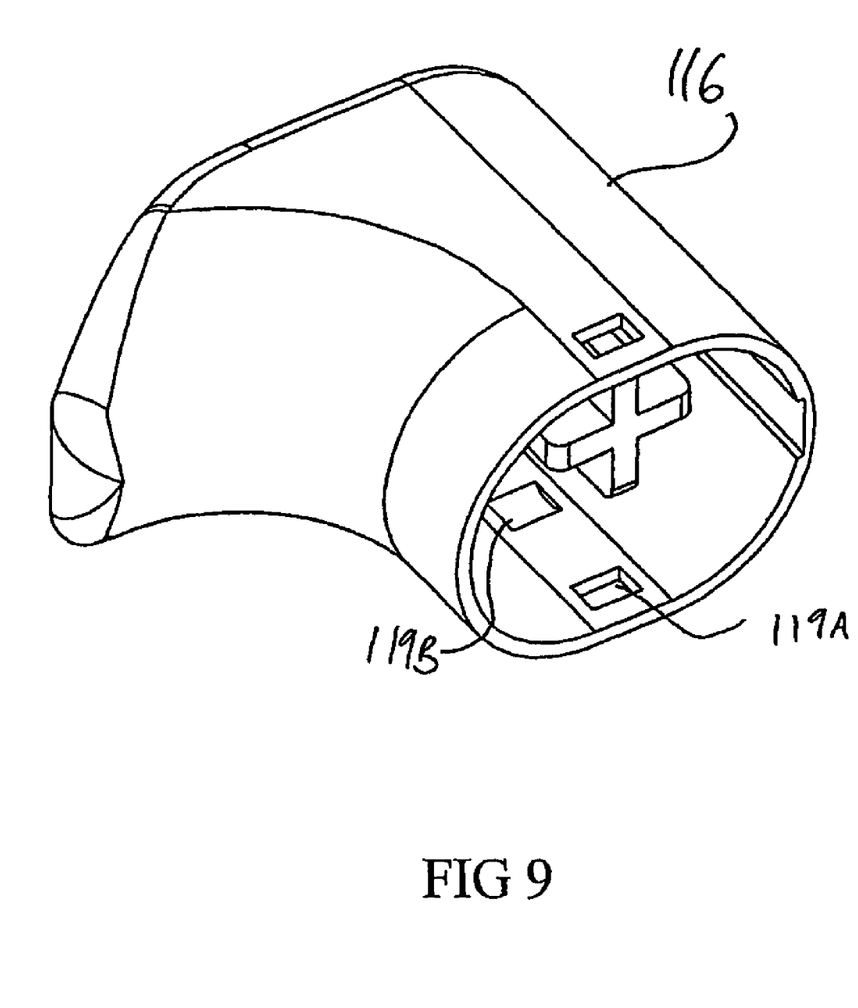
FIG. 9 is a perspective view of an end cap for use with the body part of FIG. 8.
Figure 10:
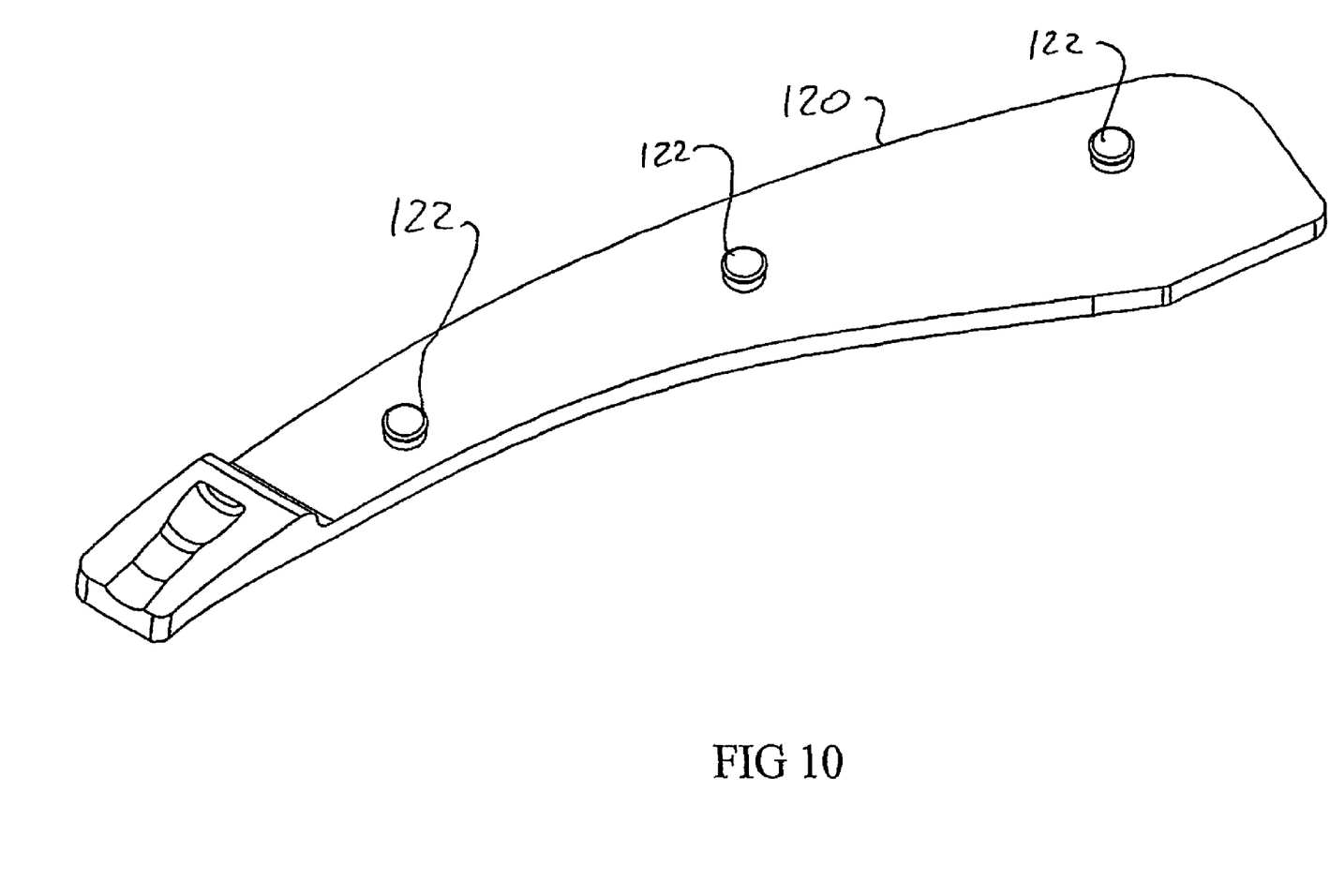
FIG. 10 is a perspective view of a snap on cover for use with the body part of FIG. 8.
Figure 11:
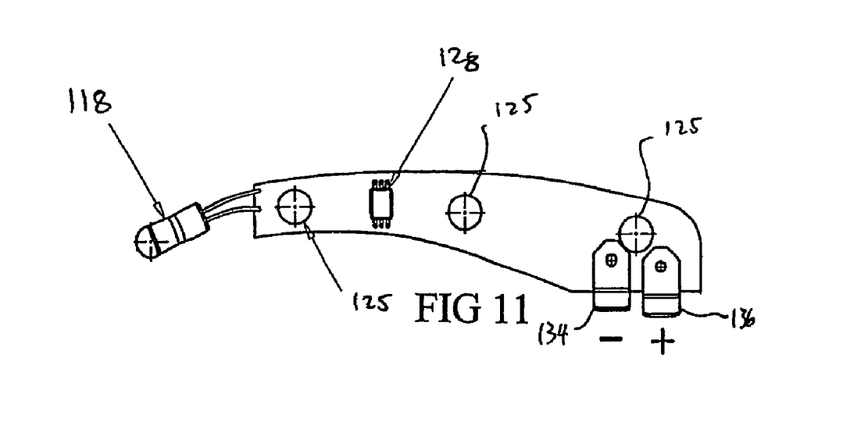
FIGS. 11 to 13 are views of a populated circuit board for use with the body part of FIG. 8.
Figure 12:
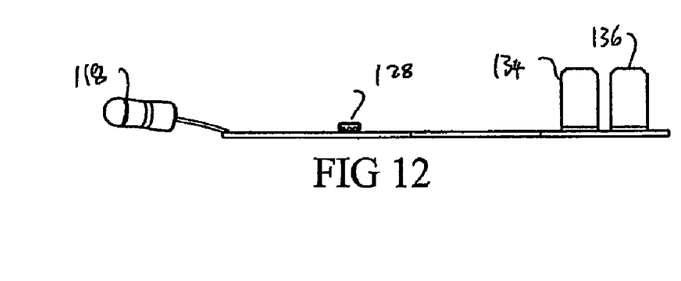
Figure 13:
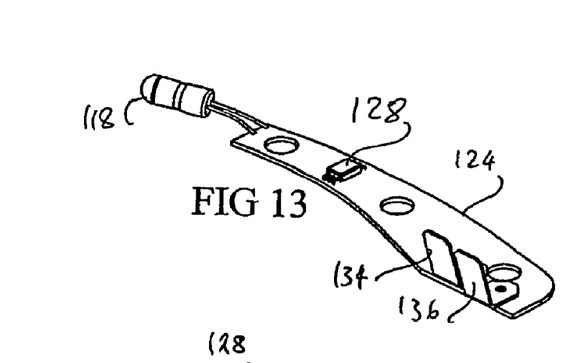
Figure 14:
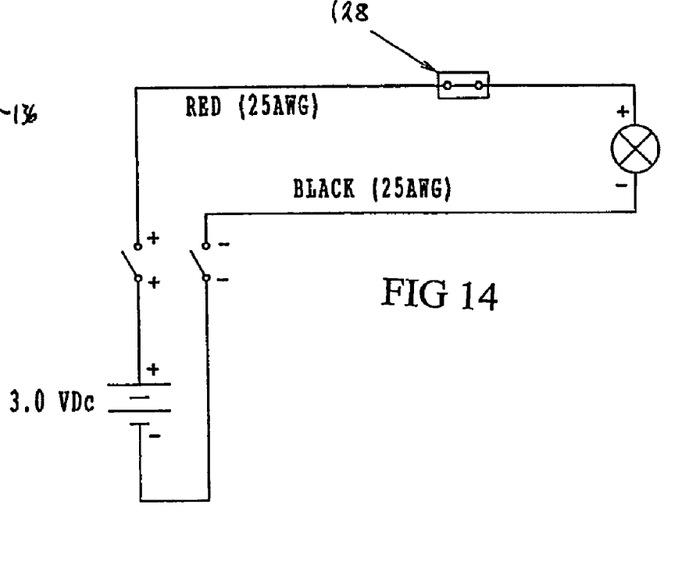
FIG. 14 is a circuit diagram of the populated circuit board of FIGS. 11 to 13.

Control means in the form of end cap 116 fits onto the end of handle 114 in either of two positions and operates to activate the light source. In the first position lug 117A engages with detent 119A. This is the "OFF" position in which the laryngoscope is supplied and remains so until the time of use. At the time of use end cap 116 is depressed to the "ON" position to cause lug 117B to engage and lock with detent 119A. This causes the batteries to contact terminals 134, 136 to activate the light source.

It is not possible to move end cap 116 back to the "OFF" position without the use of force sufficient to damage either of the lug 117A or detent 119A. This makes it difficult to re-fit end cap 116 and also provides some evidence that end cap 116 has been removed. This feature provides for removal of the batteries for separate disposal, and to discourage attempts to replace the batteries.

Figure 8:
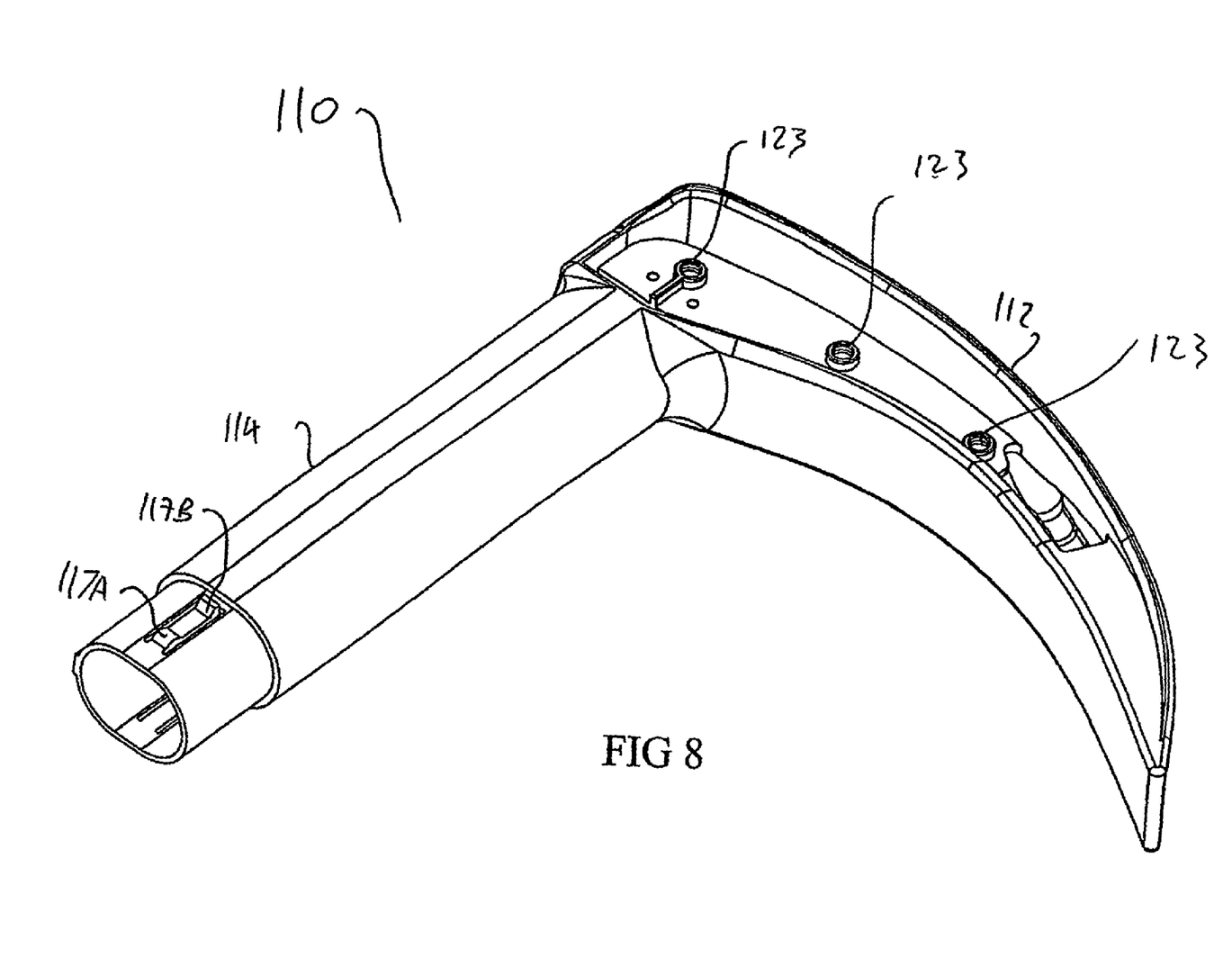
FIG. 8 is a perspective view of the body part of an alternative embodiment of a laryngoscope according to the invention.

The light source used is a xenon globe 118. A polycarbonate cap (not shown) is provided around globe 118 to prevent any glass particles from escaping in the event of a globe exploding. A lens is moulded in the end of the cap to focus light emitted from globe 118. An air gap may be provided around globe 118 to slow the rate of heating of the blade 112 in the vicinity of globe 118.

Snap on cover 120 includes snap fit lugs 122. These fit through mounting holes 125 in circuit board 124 and engage with receiving holes 123.

Figure 15:
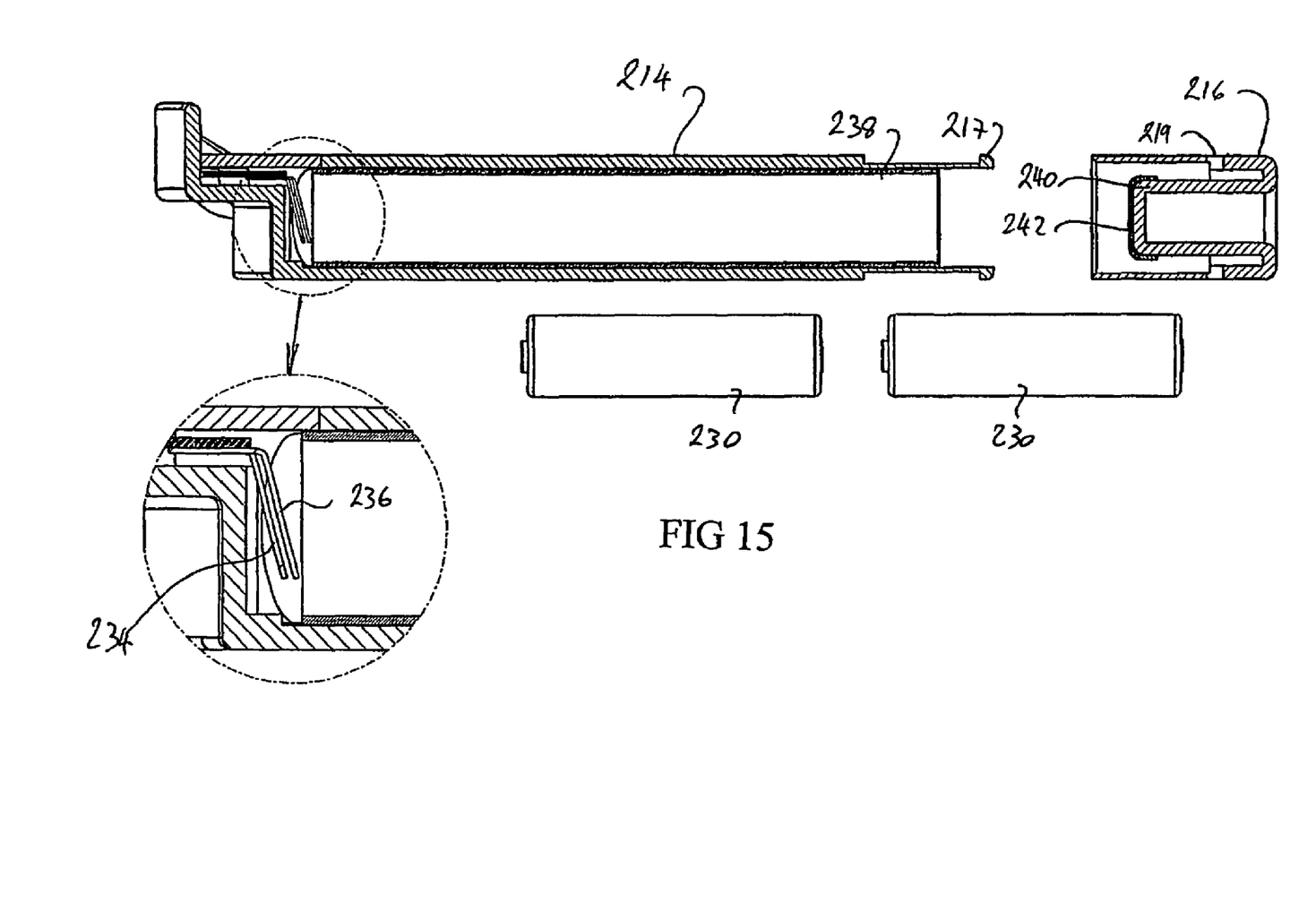
FIG. 15 is a cross section view of yet another embodiment of a laryngoscope according to the invention in the disassembled "OFF" state.
Figure 16:
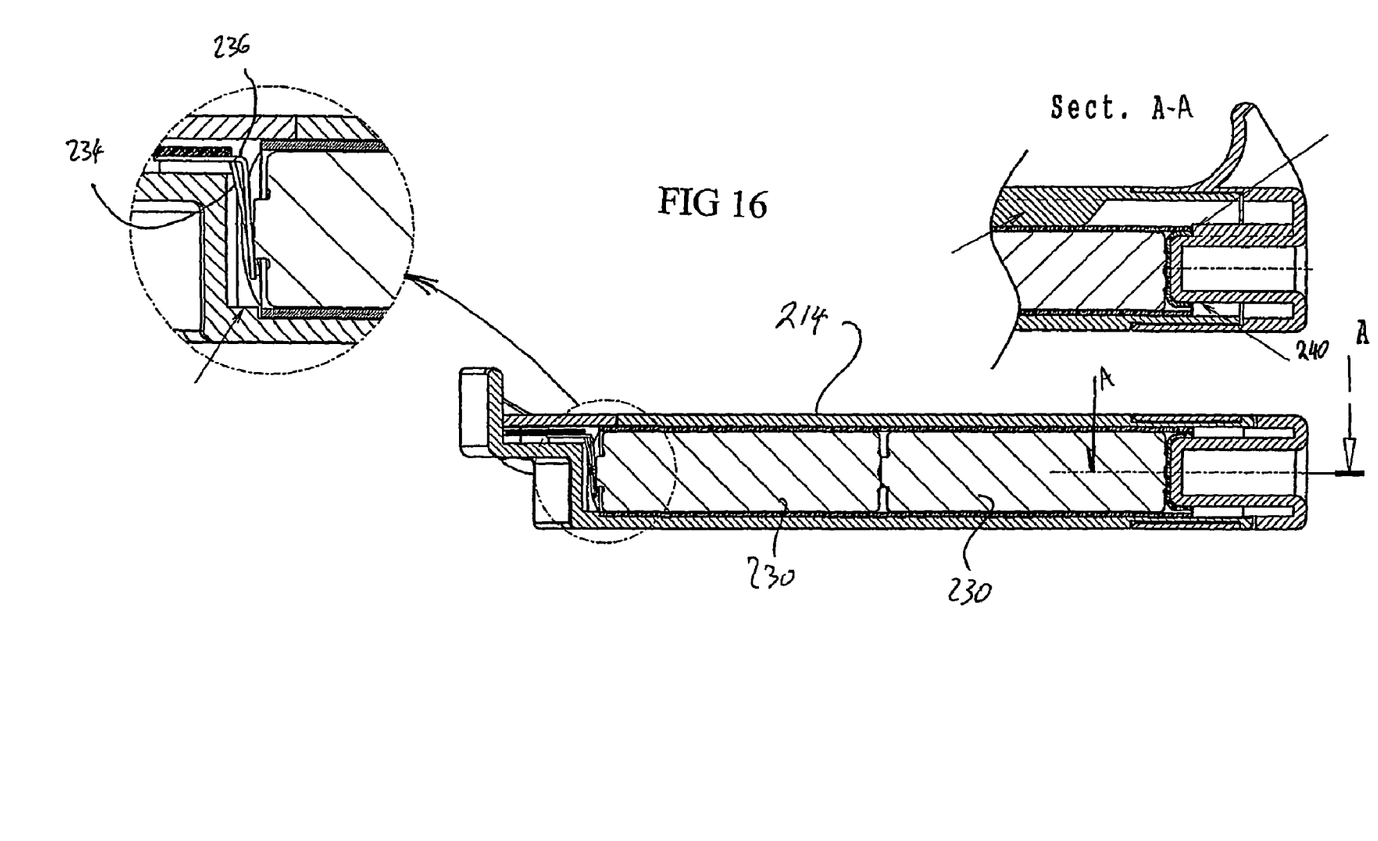
FIG. 16 is a cross section view of the laryngoscope of FIG. 15 in the assembled "ON" state.

Referring to FIGS. 15 and 16, cross sectional views of the handle part 214 of yet another alternative embodiment of laryngoscope is illustrated. In this embodiment, the laryngoscope is adapted for supply without batteries fitted. For the sake of succinctness, only differences to the second described embodiment will be explained.

FIG. 15 illustrates the "OFF" position. The end cap 216 and batteries 230 are not fitted. Aluminium sleeve 238 lines the inside surface of handle 214. Control means in the form of end cap 216 operates to activate the light source and includes a spigot 240 on which is mounted an aluminium cap 242. Battery terminals 234, 236 (see magnified section) are disposed at the mouth of sleeve 238.

FIG. 16 illustrates the "ON" position. The batteries have been fitted and end cap 216 has been pressed home so that lug 217 engages and locks with detent 219. Pressing home end cap 216 has caused movement of sleeve 238 to press against and elastically deform negative battery terminal 234. At the same time, spigot 240 pushes end cap 242 into sleeve 238 to press against batteries 230 to urge the positive end of one of the batteries against battery terminal 236 and hence complete the circuit to activate the light source (not shown).

Referring to scrap section AA, it can be seen that spigot 240 is slightly offset with respect to the central axis of sleeve 238. This ensures good electrical contact between end cap 240 and the inside surface of sleeve 238.

Again, in this third embodiment, the laryngoscope includes an end cap mounted and locked on the end of handle to retain batteries in place. It is not possible to remove end cap 216 without the use of force sufficient to damage either of the lug 217 or detent 219. This makes it difficult to re-fit end cap 216 and also provides some evidence that end cap 216 has been removed. This feature provides for removal of the batteries for separate disposal, and to discourage attempts to replace the batteries.

Laryngoscopes according to the invention may be sterilised after manufacture and despatched in sterile packaging for a single use.

In the claims which follow and in the preceding summary of the invention, except where the context requires otherwise due to express language or necessary implication, the word "comprising" is used in an inclusive sense, that is the features specified may be associated with further features in various embodiments of the invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A laryngoscope to assist tracheal intubation on a patient, comprising
    a body having a handle, and a laryngoscope blade extending from the handle, wherein the blade is permanently affixed to the handle;
    the blade and the handle being formed from hard plastic;
    an electric lighting system circuit including a light source integrated in the laryngoscope body and arranged in use to be activated to adopt an operational mode to provide illumination to the patient's throat;
    a power supply;
    control means operative to allow activation of the lighting system in the operational mode and prevent subsequent deactivation of the lighting system; and
    wherein once activated in the operational mode, the lighting system provides illumination for only a limited time.

2. The laryngoscope as claimed in claim 1, wherein the lighting system provides illumination in the operational mode for a time in order of one to three hours.

3. The laryngoscope as claimed in claim 1, wherein the control means includes an activation device that is operative to activate the lighting system to adopt the operational mode but is prevented from subsequently de-activating the lighting system.

4. The laryngoscope as claimed in claim 3, wherein the activation device is in the form of an insulating tab which provides a break in the lighting system circuit, the tab includes an end which projects outside the laryngoscope body so that it can be manually removed and wherein once removed, the lighting system circuit is established thereby causing activation of the lighting system.

5. The laryngoscope as claimed in claim 3, wherein the activation device is in the form of a switch that incorporates a part that is movable on the laryngoscope body from a first position to a second position to activate the lighting system to adopt the operational mode, but is inhibited from movement from the second position to the first position.

6. The laryngoscope as claimed in claim 5, wherein the part is formed as an end portion of the laryngoscope body.

7. The laryngoscope as claimed in claim 1, wherein the time for which the lighting system provides illumination in the operational mode is determined by the life of a power supply.

8. The laryngoscope as claimed in claim 1, wherein the control means includes a limiting device operative to establish the length of period of illumination of the lighting system in the operational mode.

9. The laryngoscope as claimed in claim 8, wherein the power supply is removable from the laryngoscope body.

10. The laryngoscope as claimed in claim 9, wherein the laryngoscope body includes a cover that allows access to a power supply, and wherein removal of the cover results in at least partial destruction of the body.

11. The laryngoscope as claimed in claim 10, wherein the cover is arranged to be snap fitted onto a portion of the laryngoscope body.

12. The laryngoscope as claimed in claim 8, wherein the lighting system is operative to adopt a test mode to allow for testing of the lighting system.

13. The laryngoscope as claimed in claim 12, wherein when in the test mode, the light source is illuminated.

14. The laryngoscope as claimed in claim 13, wherein the period the light source is able to remain illuminated in the test mode is substantially shorter than in the operational mode.

15. The laryngoscope as claimed in claim 14, further comprising an activating device that is operative to activate the lighting system to adopt the test mode.

16. The laryngoscope as claimed in claim 15, wherein the activation device is operative to activate the lighting system to adopt both the test mode and the operational mode.

17. The laryngoscope as claimed in claim 14, wherein the lighting system is operative to automatically change from the test mode to the operational mode after the lighting system has been in the test mode for a predetermined period.

18. The laryngoscope as claimed in claim 17, wherein the limiting device controls the period of illumination of the light source in the test mode and operational mode, and wherein in the test mode, the period of illumination may be interrupted and recommenced at a later time, whereas in the operational mode, the limiting device prevents interruption of the illumination period thereby limiting the lighting system to a single occurrence in operational mode.

19. The laryngoscope as claimed in claim 8, wherein the limiting device is in the form of an electronic timer connected to the lighting system circuit.

20. The laryngoscope according to claim 1, wherein the lighting system further comprises a power supply that is locatable within the laryngoscope body.

21. The laryngoscope according to claim 20, wherein the power supply is locatable in the handle of the laryngoscope.

22. The laryngoscope according to claim 20, wherein the power supply is locatable in the blade of the laryngoscope.

23. The laryngoscope according to claim 1, wherein the laryngoscope blade incorporates a cavity in which the entire lighting system is housed, the body further including a cover arranged to be locked over the blade cavity so as to prevent access to the lighting system.

24. The laryngoscope as claimed in claim 1, wherein the light source is any one of a light bulb, a LED, a halogen bulb, a krypton bulb or a xenon bulb.

* * * * *